(12) United States Patent
Otten et al.

(10) Patent No.: US 9,706,995 B2
(45) Date of Patent: Jul. 18, 2017

(54) SURGICAL CLIP AND DEVICE FOR APPLYING THE CLIP

(71) Applicants: Brigitte Otten, Schiffdorf (DE); Anja Honnefelder, Hamburg (DE); Peer Otten, Hamburg (DE)

(72) Inventors: Gert Otten, Schiffdorf (DE); Brigitte Otten, Schiffdorf (DE)

(73) Assignees: Brigitte Otten, Schiffdorf (DE); Anja Honnefelder, Hamburg (DE); Peer Otten, Hamburg (DE)

( * ) Notice: Subject to any disclaimer, the term of this patent is extended or adjusted under 35 U.S.C. 154(b) by 206 days.

(21) Appl. No.: 14/370,978

(22) PCT Filed: Feb. 7, 2013

(86) PCT No.: PCT/DE2013/000073
§ 371 (c)(1),
(2) Date: Jul. 8, 2014

(87) PCT Pub. No.: WO2013/120477
PCT Pub. Date: Aug. 22, 2013

(65) Prior Publication Data
US 2015/0148827 A1   May 28, 2015

(30) Foreign Application Priority Data
Feb. 16, 2012 (DE) .......... 10 2012 003 334

(51) Int. Cl.
*A61B 17/08* (2006.01)
*A61B 17/128* (2006.01)
(Continued)

(52) U.S. Cl.
CPC ...... *A61B 17/083* (2013.01); *A61B 17/00234* (2013.01); *A61B 17/105* (2013.01); *A61B 17/1285* (2013.01); *A61B 17/122* (2013.01)

(58) Field of Classification Search
CPC ............... A61B 17/083; A61B 17/104; A61B 17/00234; A61B 17/1285; A61B 17/122;
(Continued)

(56) References Cited

U.S. PATENT DOCUMENTS 3,510,923 A   5/1970   Blake
4,651,737 A   3/1987   Deniega
(Continued)

FOREIGN PATENT DOCUMENTS

DE   10 2004 015 223 A1   10/2005
DE   10 2004 015 224 A1   10/2005
(Continued)

OTHER PUBLICATIONS

International Search Report of PCT/DE2013/000073, mailed Sep. 9, 2013.
(Continued)

*Primary Examiner* — Christopher L Templeton
*Assistant Examiner* — Lucas Paez
(74) *Attorney, Agent, or Firm* — Collard & Roe, P.C.

(57) ABSTRACT

The invention relates to a surgical clip for minimally invasive surgery and to a device for clamping organic tissue, consisting of a first clamping bar corresponding with a second clamping bar, wherein the first clamping bar and the second clamping bar each have, on both sides on their base, shoulders for guiding them into a cartridge, and one clamping bar has a continuous retaining bore into which, in order to clamp the organic tissue, a retaining pin provided on the other clamping bar engages with a force fit and form fit, the first clamping bar (1) is mounted by means of clamp pressing in a cartridge (11), and the second clamping bar (2) with the continuous retaining bore (3) has, at its lower end, an arm (5) which, upon joining to the first clamping bar (1), slides with a form fit under the shorter first clamping bar (1)
(Continued)

with the retaining pin (4), thus clamping the organic tissue, or the first clamping bar (1) with the retaining pin (4) at its lower end has the arm (5) which, upon joining to the second clamping bar (2), slides with a form fit under the shorter second clamping bar (2) with the retaining bore (3), thus clamping the organic tissue, and a tissue clip is thus given considerable additional stability.

13 Claims, 8 Drawing Sheets

(51) Int. Cl.
    *A61B 17/10* (2006.01)
    *A61B 17/122* (2006.01)
    *A61B 17/00* (2006.01)

(58) Field of Classification Search
    CPC ............ A61B 17/072; A61B 17/07207; A61B 17/068; A61B 18/1445; A61B 2017/07214; A61B 2017/2945; A61B 2017/2927; A61B 2017/320052; A61B 2017/07271; A61B 2017/07221; A61B 2017/07281; A61B 2017/00243; A61B 2017/00026
See application file for complete search history.

(56) References Cited

U.S. PATENT DOCUMENTS

| | | |
|---|---|---|
| 7,785,335 B2 | 8/2010 | Otten |
| 8,282,654 B2 | 10/2012 | Ferrari et al. |
| 8,424,738 B2 * | 4/2013 | Kasvikis .............. A61B 17/072 |
| | | 227/176.1 |
| 2006/0047290 A1 | 3/2006 | Otten |

FOREIGN PATENT DOCUMENTS

| | | |
|---|---|---|
| DE | 20 2005 009 061 U1 | 10/2006 |
| DE | 10 2006 031 092 B3 | 1/2008 |
| DE | 10 2008 031 387 A1 | 1/2010 |
| DE | 20 2010 008 512 U1 | 11/2010 |
| DE | 20 2010 008 714 U1 | 12/2010 |
| EP | 1 611 853 B1 | 2/2007 |

OTHER PUBLICATIONS

Declaration according to Article 19, paragraph 1 PCT forwarded to the International Office of WIPO in Geneva, Switzerland by Applicants' German Attorney on Oct. 22, 2013 in PCT/DE2013/000073, along with an English translation.

* cited by examiner

SURGICAL CLIP AND DEVICE FOR APPLYING THE CLIP

CROSS REFERENCE TO RELATED APPLICATIONS

This application is the National Stage of PCT/DE2013/000073 filed on Feb. 7, 2013, which claims priority under 35 U.S.C. §119 of German Application No. 10 2012 003 334.6 filed on Feb. 16, 2012, the disclosures of which are incorporated by reference. The international application under PCT article 21(2) was not published in English.

The invention relates to a surgical clip, as it is increasingly needed in endoscopic operations in minimally invasive surgery for clamping off and interrupting soft tissue and blood vessels, and to an apparatus for applying the clip.

Known surgical clips predominantly have a U or V shape, with two clamping bars that stand opposite one another and have special shape contours. They are brought into the desired gripping and closing position with handling instruments suitable for this purpose, called applicators, with force fit. Clips made from titanium then remain in the body. They can also consist of a resorbable plastic, for example a polypeptide, which is enzymatically decomposed in the body.

A clip for closing off blood vessels is described in DE 20 2005 009 061 U1. A basic body is laid against the opened blood vessel with its inner side and closed off with multiple projecting legs affixed to the basic body in flexible manner, by means of bending these legs. In addition to complicated handling, this clip does not offer sufficient safety to prevent injury of tissue.

DE 10 2008 031 387 A1 discloses a medical clip for closing off a tissue opening. Two gripping arms mounted axially on an axis of rotation, the ends of which arms are angled away toward one another, in each instance, are given the required gripping force for closing off the tissue opening, in the case of reciprocal engagement, by means of a spring force or by means of an engagement mechanism. The tissue is essentially gathered. Targeted clipping is possible only in restricted manner with this technical solution. Likewise, the area of application is limited, and blood vessels, for example, are excluded.

A surgical clip for clamping off and interrupting blood vessels is evident from DE 10 2006 031 092 B3; it consists of two arms that are connected with one another by way of a spring element and cross one another, which carry clamping jaws at their ends, in each instance. In order to allow reproducible and non-displaceable placement of the clip, the arms have openings on both sides, transverse to their longitudinal direction, into which pin-shaped or stud-shaped fixation elements can engage. This technical solution is characterized by a very complicated tensioning mechanism and uncertain clipping.

A clip intended as an implant is disclosed by DE 20 2010 008 512 U1. Two clip branches are held at their first free ends by means of a spring-elastic element, lying against and parallel to one another, and have a second end, whereby the two ends are connected, in each instance, by means of sections configured to intersect. To apply the clip in an application position, the second ends are grasped by clip application forceps and brought close to one another counter to the spring force of the spring-elastic element. In order to achieve a precise closing force, the clip branches have contact elements configured complementary to one another. This solution is not suitable for minimally invasive surgery. Because of the shear effect that is present, there is furthermore the risk that the branches will be pressed apart from one another during their use.

A further surgical clip is described by DE 20 2010 008 714 U1. It consists of two clip branches, the first free ends of which are held parallel to one another by means of the predetermined closing force of a spring-elastic element, while the second also free ends are affixed to the spring-elastic element. In order to apply the clip, the second free ends are grasped with a gripping tool specifically intended for this purpose, and brought into contact with one another, so that the clip branches open and can be applied. The clip is positioned by means of relieving the stress on the second free ends. Production of this clip appears to be complicated and particularly elaborate.

DE 10 2004 015 224 A1 describes a surgical clamp made of resorbable material for clamping off organic tissue, particularly blood vessels; this clip is formed from two shanks disposed in V shape, and one shank has a holding pin at its end, which pin engages into a recess provided on the end of the other shank and is fixed in place there, in order to clamp off the organic tissue. Its use for axial clipping restricts the use of this clip.

For use in open surgery, the surgical clamp that is evident from DE 10 2004 015 223 A1 is suitable. The organic tissue to be connected can be positioned between two clamping bars disposed parallel to one another, and afterward, it can be fixed in place by means of pins that are disposed on a clamping bar, transverse to the longitudinal axis of the latter, and engage into matching bores of the other clamping bar.

U.S. Pat. No. 4,651,737 discloses an apparatus for clamping off organic tissue, particularly blood vessels, using a set of clamping rods. A clamping rod disposed at the distal end is releasably connected with an application crosspiece by means of a stud connection. On this crosspiece, the other clamping rod can be pushed against the clamping rod disposed on the distal end, in the horizontal position, clamping off the organic tissue, and can be released from the application crosspiece together with this rod and the clamped-off organic tissue.

However, this technical solution is connected with the problem that the clamping rods have a predetermined and unchangeable distance relative to one another while closing, with their clamping crosspieces, which are partly interconnected, because they are pushed not against one another, but in the end phase one on top of the other, and therefore produce a shear/clamping effect in the organic tissue, with the great risk of injury to the tissue, going as far as unintentional cutting of tissue. Therefore infinitely adjustable clamping off of organic tissue, as a function of the compression pressure, is objectively not possible. In this regard, the technical solution described in U.S. Pat. No. 4,651,737 does not permit the clamping rods to be brought toward one another in infinitely adjustable manner, to clamp off the tissue. Clamping-off takes place without being able to take the type of tissue and the other existing conditions into account. The gap that forms from the clamping rods being pushed one on top of the other has an unchangeable size, so that the risk exists that tissue, particularly small blood vessels, can be clamped off only insufficiently, and that bleeding during an operation can be the result.

With the goal of overcoming the stated problems, EP 1 611 853 B1 proposes a surgical apparatus for clamping off organic tissue, particularly blood vessels, using a set of clamping bars disposed on an application crosspiece.

The clamping bars have at least one guide pin at their base, on both sides, in each instance, for positioning and for horizontal displacement in the apparatus. To produce a tissue clamp, the clamping bar disposed at the distal end has a holding bore at its base, which corresponds to the holding pin provided at the base of the other clamping bar and, after the clamping bars have been pushed together by means of a plunger, clamping the tissue in the applicator, forms the tissue clamp. In this connection, the guide pins are dimensioned in such a manner that they shear off if the force exertion required for clamping off the tissue is exceeded, and the tissue clamp formed can then easily be pushed away from the application crosspiece by means of the centrally positioned plunger.

Use of this technical solution demonstrates easy handling of the applicator and allows safe fixation of the clamped-off tissue in the clamp. It has also been shown, however, that the tissue clamp produced in this way still does not satisfy the increased demands in its longitudinal direction, particularly with regard to the compression pressure between the clamping bars required for great stability of the tissue clamp.

The tissue to be clamped is very non-homogeneous in terms of its structure, for example blood vessels demonstrate a greater clamping resistance than loose connective tissue. Depending on the tissue resistance at a specific point and the clamping pressure exerted, it cannot be precluded that the clamping bars move away from one another in a V shape as the result of insufficient stability of the holding pin of the clamp, and can thereby lead to partial or complete loss of the function of the clip.

It is therefore the task of the invention to make available a significantly improved clip, which allows stable and torsion-resistant application while maintaining tissue-protecting use, and thereby allows permanent and extensively homogeneous tissue compression between the clamping bars, and ensures great closure safety of the tissue clamp with regard to both a rotation-stable position and in the longitudinal direction of the tissue clamp.

Furthermore, the task of the invention consists in making available an apparatus that allows safe application of the clip, with simple handling.

According to the invention, the task is accomplished by a surgical clip for minimally invasive surgery, for clamping off organic tissue, which consists of a first clamping bar corresponding to a second clamping bar, wherein the first clamping bar and the second clamping bar, at their base, on both sides, have shoulders for being guided in a cartridge, in each instance, and one clamping bar has a continuous holding bore into which a holding pin provided on the other clamping bar engages for clamping off the organic tissue, with force fit and shape fit, wherein the first clamping bar is mounted in the cartridge by means of clamping pressure, and the second clamping bar having the continuous holding bore possesses a shank at its lower end, which shank, during joining together with the first clamping bar, clamping off the organic tissue, pushes itself, with shape fit, under the shorter first clamping bar having the holding pin, or the first clamping bar having the holding pin has the shank, at its lower end, which shank, during joining together with the second clamping bar, pushes itself, with shape fit, under the shorter second clamping bar having the holding bore, or the second clamping bar, which has both the holding pin and the shank, during joining together with the first clamping bar, clamping the organic tissue, pushes itself, with shape fit, under the shorter first clamping bar having the holding bore, and thereby a tissue clamp is given significant additional stability.

Furthermore, the task is accomplished by means of an apparatus for applying a surgical clip that is formed from a first clamping bar corresponding to a second clamping bar, having the stated characteristics, in each instance, wherein the apparatus is configured as a cartridge that accommodates this clip, the cartridge has grooves that run in the longitudinal direction, on both sides, open toward the distal end of the cartridge, for mounting and guiding the shoulders of the first and second clamping bar and a plunger, as well as at least one recess for accommodating the clamping bar, the first clamping bar is positioned on the distal end of the cartridge by means of clamping pressure, the plunger is mounted in the cartridge for displacement of the second clamping bar and for ejection of the tissue clamp, and the cartridge has means for a releasable connection with an applicator at the proximal end.

The invention is associated with the particular advantage that while the clip is still open, the first clamping bar mounted at the distal end of the cartridge, with pressure clamping in the guide groove of the cartridge, can temporarily be used as a hook for presentation of the tissue structure to be clipped. Only because of the safe hook function of this first clamping bar does it become possible at all to search for and establish the ideal position for clipping in the tissue while the clip is still open.

The second clamping bar can be brought together with the first clamping bar in infinitely adjustable manner, in one plane, in controlled manner in every situation, whereby the tissue is squeezed in sufficiently gentle manner, but not crushed, precisely at the desired location, by means of the infinitely adjustable pressure clamping, and thereby perfusion in the organic tissue is interrupted.

This new possibility of setting a clip precludes incorrect placement of the clip and thereby serious consequences for the patient. The tissue clamp, with its great closure safety, is a tissue clamp that is particularly suitable for minimally invasive surgery, because setting of the clipping takes place, in every phase, with an unrestricted view of the OP field, and thereby incorrect placement of the clip is excluded.

The holding pin and holding bore are structured to correspond to one another with their non-circular shape and their cross-section. The clip according to the invention makes it possible for the tissue to be clamped off exclusively by means of an infinitely adjustable pressure clamping mechanism, and for the two clamping bars with the clamped-off tissue to be held in a position that is both torsion-resistant and permanently stable in the longitudinal direction of the tissue clamp.

The holding pin is particularly relieved of bending stress by means of the additional shank that pushes itself, with shape fit, under the shorter corresponding clamping bar when the organic tissue is clamped off, the parallelity of the clamping bars that remains necessary is guaranteed in every phase of the clipping process, and thereby the tissue clamp is given the required great stability.

The stability of the tissue clamp is thereby guaranteed not only by the shank of the longer clamping bar, which shank is placed under the shorter corresponding clamping bar, with shape fit, but also by the clamping pressure of the holding pin that is relieved of bending stress. Bending open of the two clamping bars during closing of the clip and in its closed state is thereby prevented. The clip maintains its stability until wound healing is complete.

The invention furthermore allows flexible adaptation to different thicknesses of the tissue.

The clip according to the invention can be produced in an extremely delicate version and therefore possesses an extreme spatial mobility that is very important for minimally invasive surgery.

The invention thereby fulfills an urgent need that exists in minimally invasive surgery for a maximum of safety when setting the clip, and, at the same time, guarantees the greatest possible safety for patient and physician. Therefore significant technical progress is associated with the invention.

In a particular embodiment of the invention, the shoulders of the clamping bar are configured to be flattened toward the distal end, over their entire length or only in part.

According to another embodiment, the clamping surfaces of the clamping bars are roughened or configured in corrugated shape.

According to another embodiment, the clamping surfaces of the first and of the second clamping bar are configured in step shape, corresponding to one another.

A particularly preferred embodiment provides that the shank of the clamping bar has a length that corresponds at least to the longitudinal width of the corresponding first or second clamping bar at its base.

It is advantageous if the width of the shank corresponds to the width of the bed of the cartridge.

According to another embodiment of the invention, the shoulders of the first clamping bar have a ribbing that runs perpendicular to the longitudinal axis of the cartridge.

According to a particularly preferred embodiment of the invention, the clamping pressure of the first clamping bar is brought about by means of the reduction in the clear width between the guide grooves that runs in the direction of the distal end of the cartridge and/or by means of the ribs of the shoulders of the first clamping bar that engage into recesses of the cartridge.

The shoulders of the first and of the second clamping bar preferably consist of a resorbable material and preferably have an elasticity such that the tissue clamp that is formed can be ejected by means of pressing pressure, even with rigid distal ends of the cartridge, without damage.

According to another embodiment of the invention, the shoulders of the first and of the second clamping bar consist of a non-elastic material, and the distal end of the cartridge is configured to be elastic, so that ejection of the tissue clamp without damage is possible.

Particularly preferred embodiments of the apparatus according to the invention provide that the clear width between the guide grooves decreases in the direction of the distal end of the cartridge and/or the guide grooves of the cartridge have recesses for accommodating the ribbing at the distal end and/or that the distal end of the cartridge and/or the shoulders consist of an elastic material.

According to another embodiment, the means for a releasable connection with the applicator consists of a stop and a fixation element provided at the lower end of a sheathing tube section of the cartridge for accommodation of the applicator, by means of a bayonet closure.

According to another embodiment, the means for a releasable connection with the applicator are engagement elements.

Preferably, the plunger has a fixation element on its underside, which engages into corresponding recesses when the apparatus is handled, which recesses are provided in the bottom of the sheathing tube section, at a distance from one another in the longitudinal direction.

In the following, the invention will be explained in greater detail using drawings that show the surgical clip in a significantly enlarged and schematic representation. The drawings show.

Figure 1:
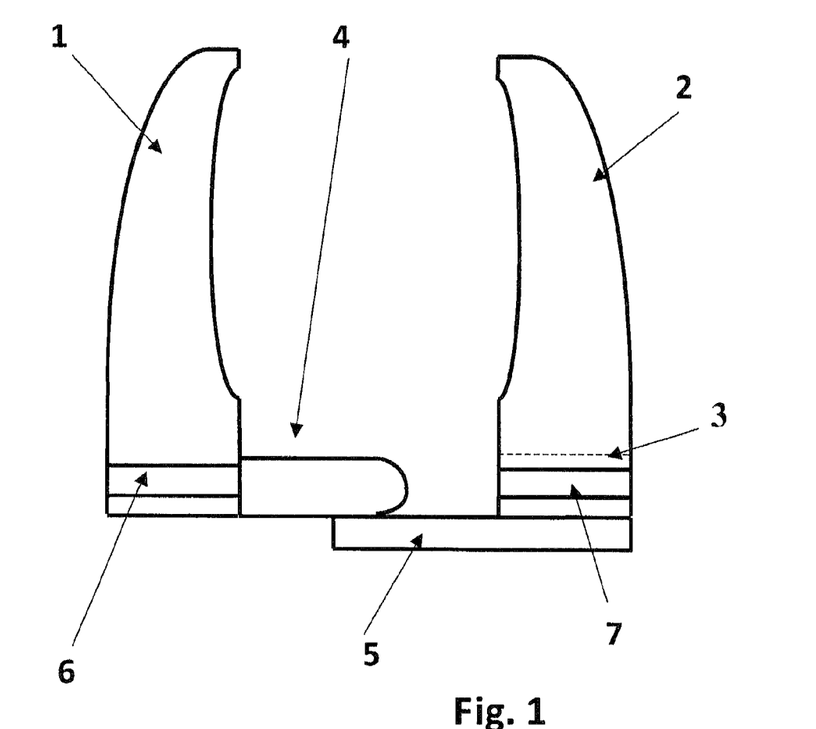
FIG. 1 the side view of the clip in a schematic diagram.
Figure 1A:
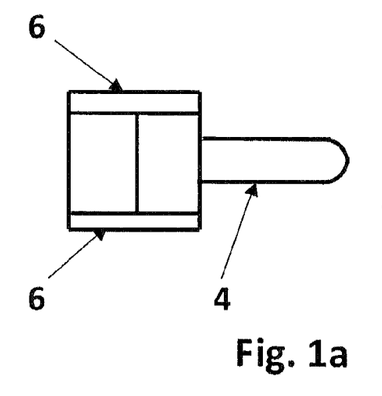
FIG. 1*a* the top view of the clamping bar of FIG. 1 with holding pin.
Figure 1B:
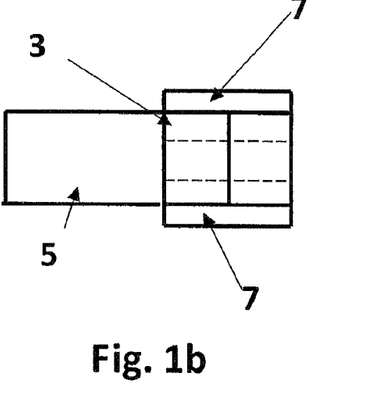
FIG. 1*b* the top view of the clamping bar of FIG. 1 with holding bore.

As can be seen in FIG. 1 as well as in FIGS. 1*a* and 1*b*, the clip according to the invention consists of the first clamping bar 1 and second clamping bar 2, which correspond to one another, the clamping surfaces of which bars are configured to be concave, and, if necessary, can also have a roughened, corrugated or convex surface. The clamping bars 1, 2 can also possess clamping surfaces configured in planar shape. The shoulders 6 and 7 are provided at the base of the clamping bars 1, 2, which consist of a resorbable material of a known type; the clamping bars 1,2 are horizontally guided in matching grooves 13, 22 of the cartridge 11 used for their application by means of these shoulders, after the clamping bars 1, 2 have previously been introduced into the cartridge 11 through matching insertion openings 21 and brought into position.

The shank 5 disposed at the base of the second clamping bar 2, which preferably fills the width of the bed 12 of the cartridge 11, is essential to the invention. The first clamping bar 1 having the holding pin 4 is positioned at the distal end of the cartridge 11, not shown here, by means of pressure clamping. In order to clip tissue, the second clamping bar 2 is pushed toward the distal end, whereby the holding bore 3 of the second clamping bar 2 engages around the holding pin 4 of the first clamping bar 1, and the shank 5 pushes itself flush under the shorter first clamping bar 1. When the second clamping bar 2 is pushed against the first clamping bar 1 in order to clip tissue, the shank 5 slides on the bed 12 (FIG. 7 and FIG. 9) of the cartridge 11 not shown here. The shank 5 allows rotation-free and tilt-free advancing of the second clamping bar 2 and thereby guarantees the most stable precision when bringing the first clamping bar 1 and the second clamping bar 2 together, until the tissue clamp is formed. The shank 5 advantageously possesses a length that corresponds at least to the longitudinal width of the corresponding clamping bar 1, 2, in each instance.

The holding bore 3 has a shape that deviates from a circle, in its cross-section, for ensuring a rotation-stable position of the tissue clamp.

As soon as the pressure exerted by the plunger 14, not shown here, on the grasped tissue and the clamping bar 1, by way of the second clamping bar 2, exceeds the clamping pressure of the cartridge 11 on the shoulders 6, 7 of the first clamping bar 1, the tissue clamp formed by means of the force fit and shape fit of the holding pin 4 in the holding bore 3 is released out of the cartridge 11 by means of the plunger 14. It is important, in this connection, that a resorbable material is used for the shoulders 6; 7 of the clamping bars 1, 2, the elasticity of which allows ejection of the tissue clamp formed, from the distal end of the cartridge, without damage, even when the ends of the cartridge 11 are configured to be rigid. If a non-elastic material is used for the shoulders 6, 7 of the clamping bars 1 and 2, elastic configuration of the distal ends of the cartridge 11 allows ejection of the tissue clamp without damage. The elasticity of the resorbable material and the elasticity of the distal ends of the cartridge can also be coordinated with one another, in order to guarantee ejection of the tissue clamp without damage.

The shank 5 has particular importance from a medical, particularly a surgical aspect. It gives the finished tissue clamp additional mechanical stability, above all, in addition to supporting the rotationally stable position, along with great security in the longitudinal direction of the tissue clamp, with simultaneously secure fixation of the tissue structure. This additional stability is of decisive importance when clips having a greater length of the clamping bars 1, 2 are used. In general, clips having a length of the clamping bars of 5 mm to 20/25 mm are used.

The tissue clamp, with the shank 5 positioned under the first clamping bar 1 and the shape-fit and force-fit connection of the holding pin 4 in the holding bore 3, has a stable two-point mounting that continuously exerts the same clamping pressure on the tissue between the first clamping bar 1 and the second 2.

Figure 2:
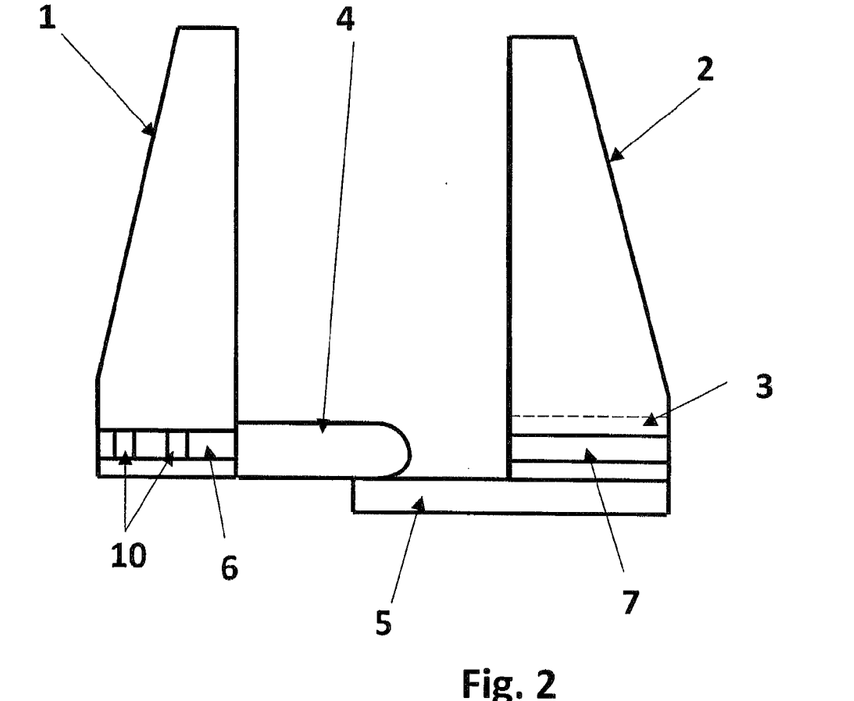
FIG. 2 the side view of a special embodiment of the clip in a schematic diagram.
Figure 2A:
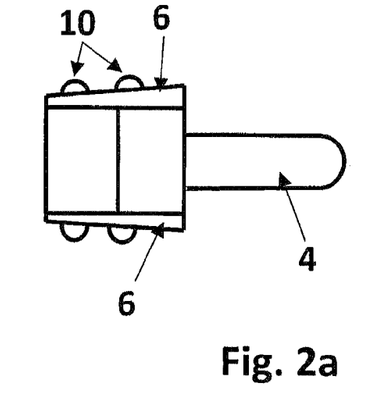
FIG. 2*a* the top view of the clamping bar of FIG. 2 with holding pin.
Figure 2B:
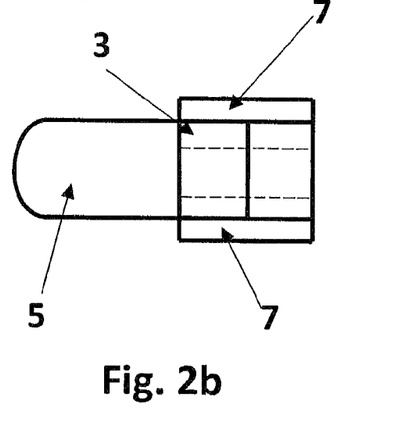
FIG. 2*b* the top view of the clamping bar of FIG. 2 with holding bore.

FIGS. 2, 2a, and 2b show a special embodiment of the invention in a side view and top views. As is evident from FIG. 2a, the shoulders 6 of the first clamping bar 1 are flattened toward the distal end of the bar, and here have two ribs 10, in each instance, that run vertically on each side. However, the clamping bar 1 can also be provided with shoulders 6 having only one rib 10 or more than two ribs 10 on each side. The cartridge 11, corresponding to the ribs 10, possesses corresponding recesses on its two inner surfaces. However, it is also possible that the shoulders 6, 7 have recesses for the ribs that are configured corresponding to them in the guide grooves. The ribs 10 fix the first clamping bar 1 in place, by themselves or in addition to the pressure clamping exerted by the cartridge 11. The stable and tilt-free seat of the first clamping bar 1 is supported in this manner. The ribs 10 thereby, at the same time, support the use of the first clamping bar 1, which is used in surgery, as a fixed, tilt-free hook for presentation of the tissue to be clipped while the clip is open; this is connected with an outstanding increase in efficiency in terms of the precision and safety of the clipping process.

When the tissue clamp is closed, the bending stress of the holding pin 4 is significantly reduced, if not actually eliminated, by the shank 5, which engages under the corresponding clamping bar; this is connected with a significant increase in the stability of the tissue clamp.

For the hook function, it is of particular importance that the bending stress of the holding pin 4 is significantly reduced or actually eliminated.

For use of a clip configured in this manner, it is advantageous if the clear width between the guide grooves 13, 22 decreases toward their distal end and/or the lateral parts of the cartridge are configured to be elastic toward their distal end.

The degree of the infinitely adjustable clamping of the tissue can be varied by means of the contact angle of the clamping surfaces of the shoulders 6, 7 and the corresponding groove 13, 22 of the cartridge 11 during its production, and adapted to the desired press-down pressure on the clamping bars 1, 2, in each instance. Furthermore, the degree of the pressure clamping can be adjusted by means of the selection of a material for the clamping bars 1, 2 and the cartridge 11, having a suitable modulus of elasticity.

Figure 7:
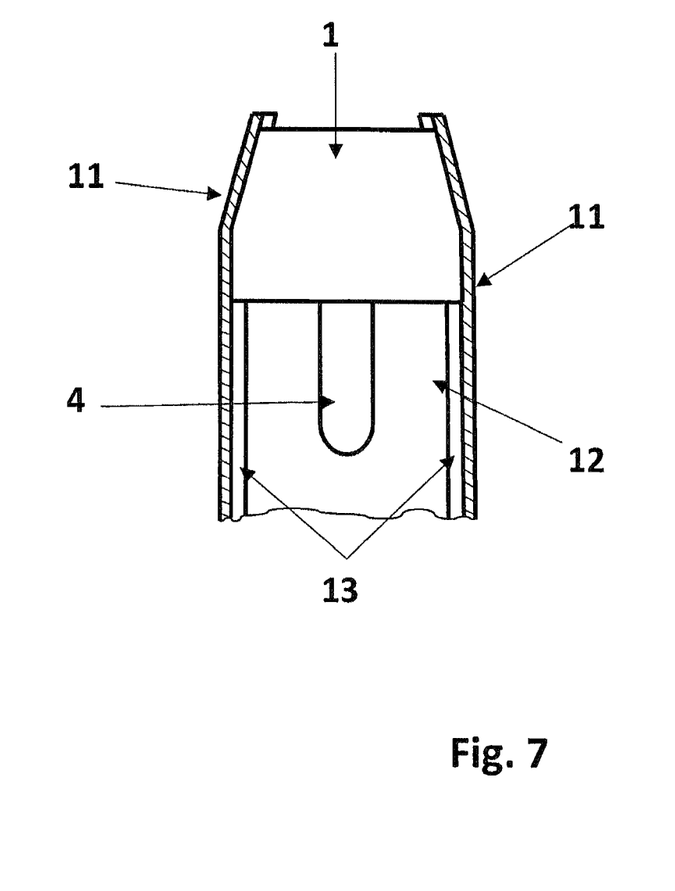
FIG. 7 partly in longitudinal section, the schematic diagram of a clamping bar in a cartridge.

FIG. 7, in a partial longitudinal section and a schematic diagram, shows a first clamping bar 1 positioned at the distal end of a cartridge 11, with its partially flattened shoulders. The distal end of the cartridge 11 is configured to be elastic and has a clear width of the guide grooves 13 that decreases toward the distal end. The cartridge 11 has an ejection channel that reaches over a part or the entire width of the shoulders of the first clamping bar 1, on both sides. In contrast to this, in the case of known technical solutions, the guide pins used to guide clamping bars must be sheared off in order to eject the tissue clamp.

Figure 3:
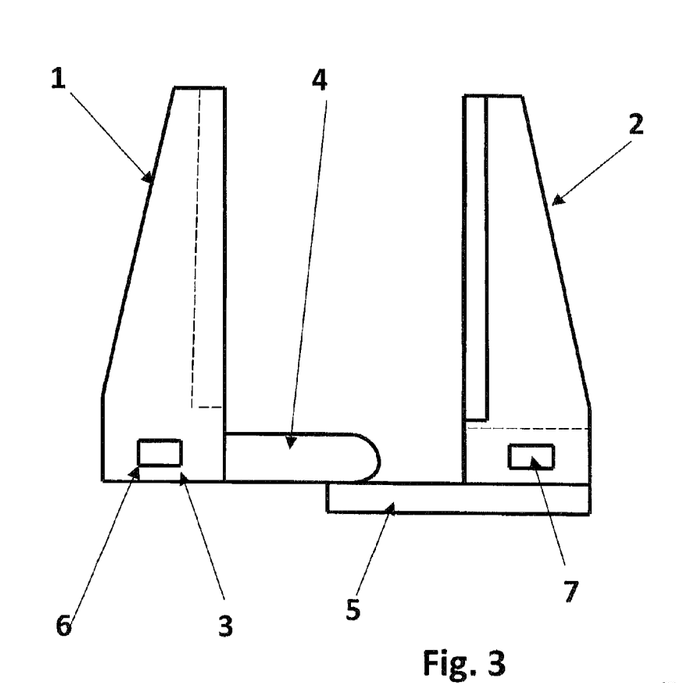
FIG. 3 the side view of another special embodiment of the clip in a schematic diagram.
Figure 3A:
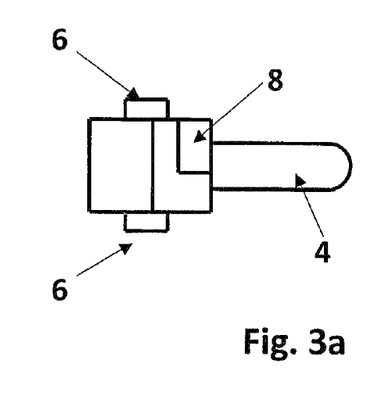
FIG. 3*a* the top view of the clamping bar of FIG. 3 with holding pin.
Figure 3B:
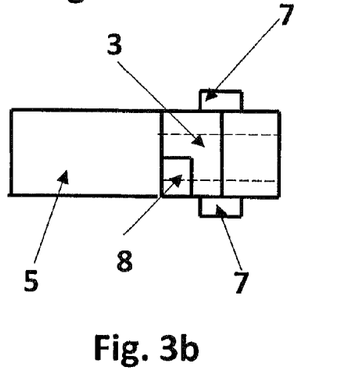
FIG. 3*b* the top view of the clamping bar of FIG. 3 with holding bore.

A further embodiment of the invention is evident from FIGS. 3, 3a, and 3b. The shoulders 6, 7 do not extend, in each instance, over the entire width of the base of the clamping bars 1, 2. Here, the clamping surfaces 8 of the clamping bars 1, 2 are configured in corresponding step shape, and in this regard engage into one another when the tissue is clipped. Shoulders 6, 7 that extend over the entire longitudinal width of the clamping bars 1, 2 can also be divided.

Figure 4:
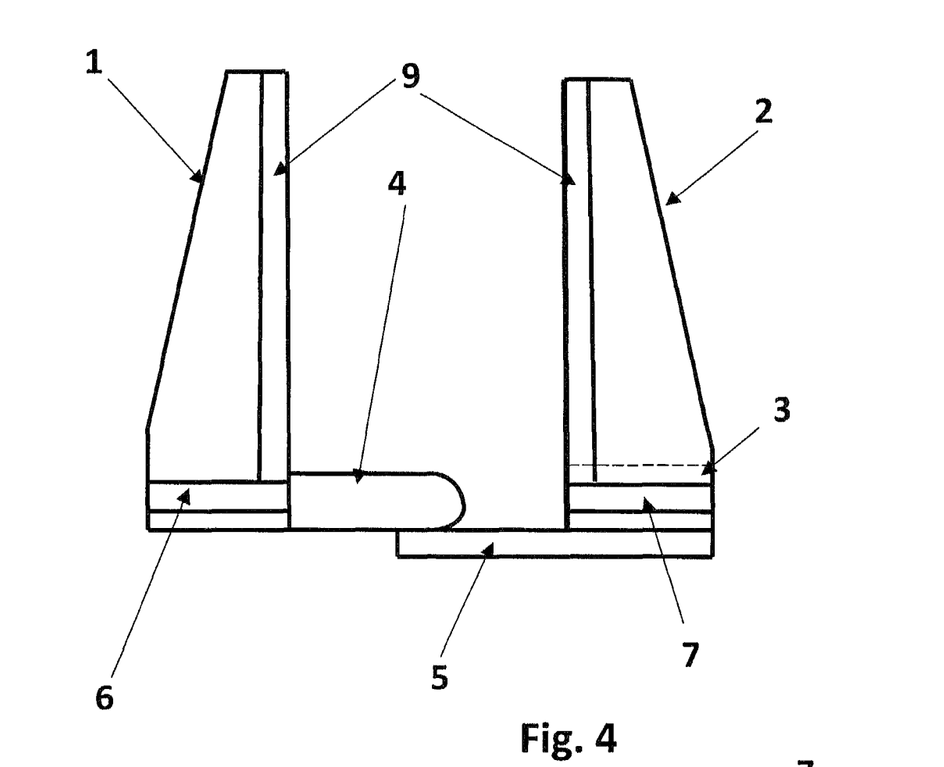
FIG. 4 the side view of another special embodiment of the clip in a schematic diagram.
Figure 4A:
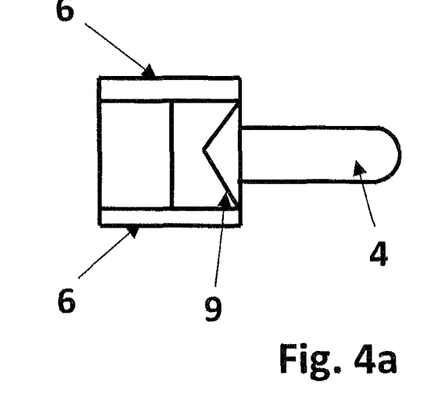
FIG. 4*a* the top view of the clamping bar of FIG. 4 with holding pin.
Figure 4B:
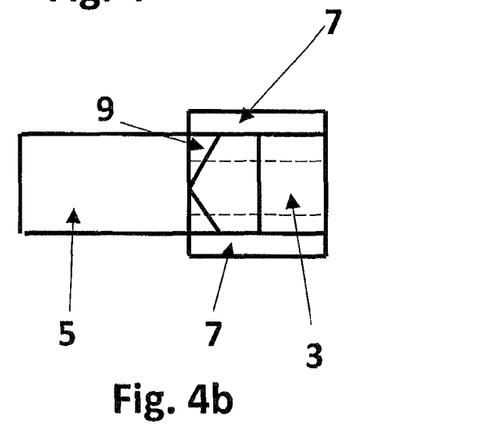
FIG. 4*b* the top view of the clamping bar of FIG. 4 with holding bore.

FIGS. 4, 4a, and 4b also show an embodiment of the invention having special shaping of the clamping surfaces 9 of the clamping bars 1, 2. The clamping surface 9 of the second clamping bar 2, which is configured as an obtuse angle in cross-section, engages into a correspondingly configured shape of the cross-section of the clamping surface 9 of the first clamping bar 1 for clipping. Such a configuration of the clamping surfaces 9 supports secure fixation of the tissue, above all if, in addition, these surfaces 9 have a roughened surface.

Figure 5:
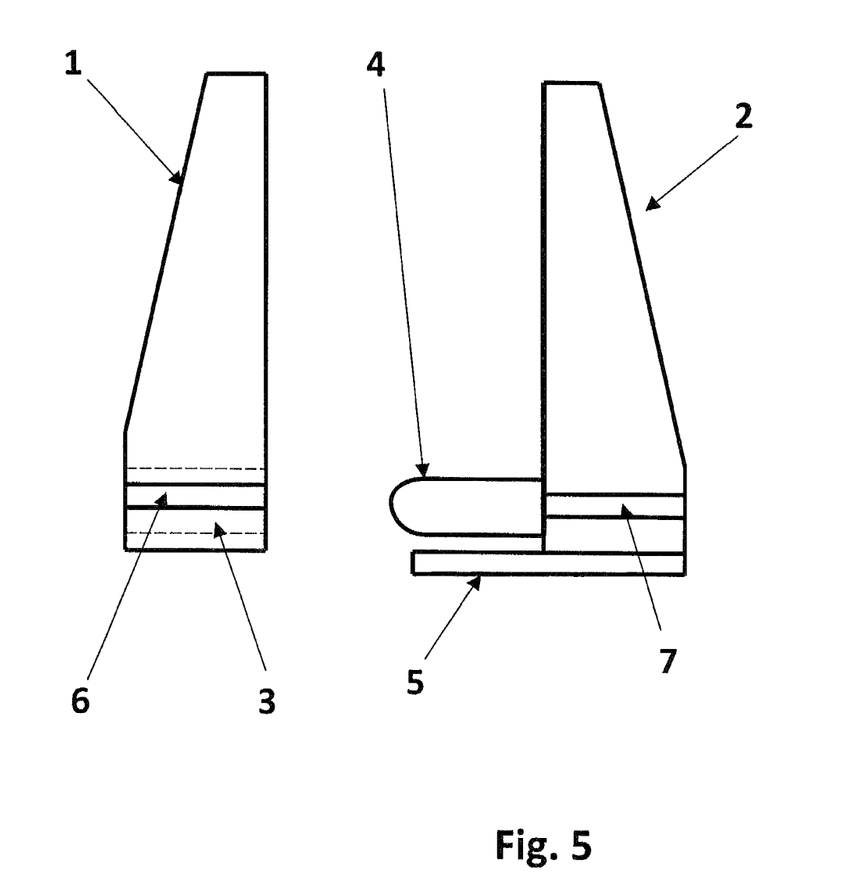
FIG. 5 the side view of another embodiment of the clip.

As is evident from FIG. 5, the holding pin 4, together with the shank 5 that is essential to the invention, which preferably has the same width as the second clamping bar 2, can also be provided on the latter, just like the first clamping bar 1 can have both the holding pin 4 and the shank 5, and the clamping bar 2, which is then shorter, can have the holding bore 3.

Figure 6:
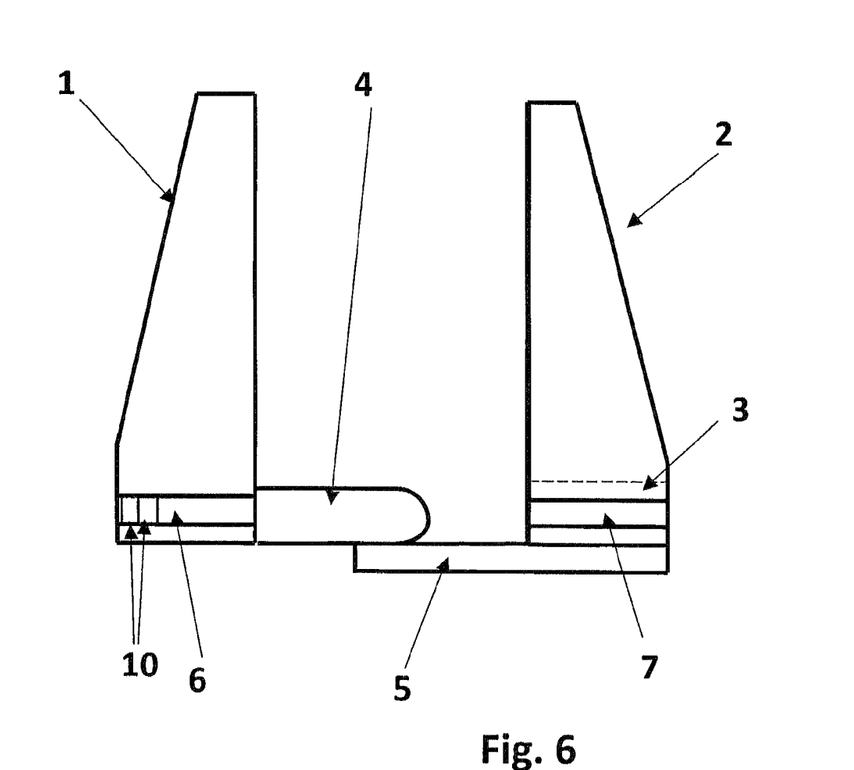
FIG. 6 the side view of another embodiment of the clip.
Figure 6A:
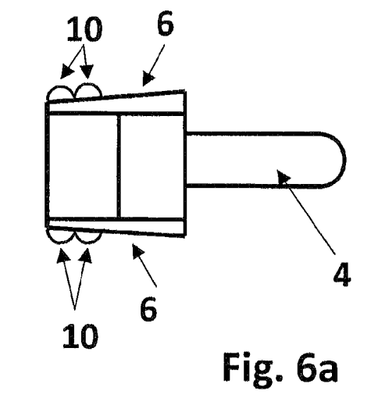
FIG. 6*a* the top view of the clamping bar of FIG. 6 with holding pin.
Figure 6B:
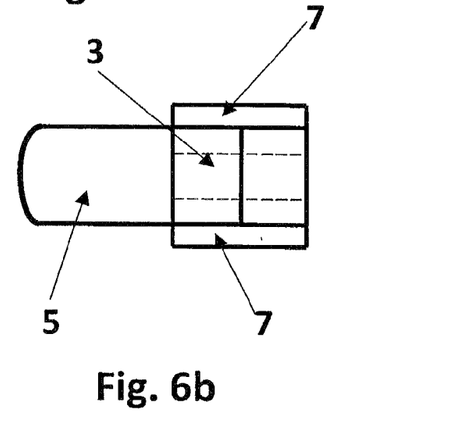
FIG. 6*b* the top view of the clamping bar of FIG. 6 with holding bore.

FIGS. 6, 6a, and 6b show another embodiment of the invention. The shoulders 6 of the first clamping bar 1 have a vertically running ribbing 10 in addition to their flattening that runs toward the distal end, this ribbing consisting of a rib or multiple ribs. The lateral parts of the cartridge 11 possess matching accommodations for the ribbing 10, in each instance.

It is understood that the clip according to the invention can contain the technical characteristics shown in FIGS. 1 to 7 in different combinations. For example, the ribbing 10 can also be provided on the non-flattened shoulders 6 and 7 of the clamping bars 1, 2. The shank 5 can also be disposed on the first clamping bar 1. When the clamping bars 1 and 2 are brought together, the second clamping bar 2, which is then shorter in this case, pushes itself flush over the shank 5 with its lower end, and in this connection clamps off soft tissue or blood vessels or interrupts them.

Figure 8:
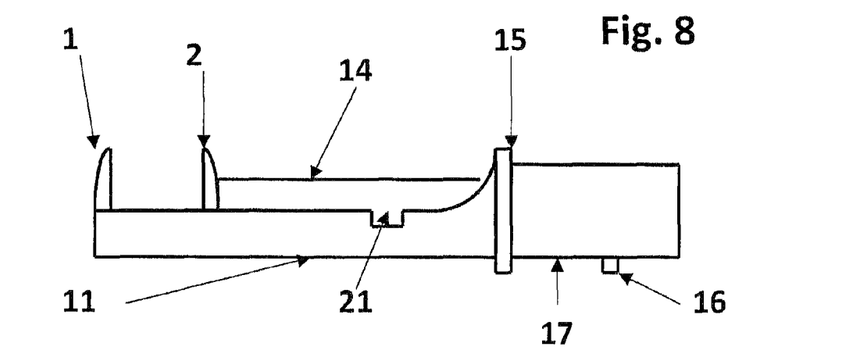
FIG. 8 the side view of a cartridge with inserted clip in a schematic diagram.

FIG. 8 shows a schematic diagram of a cartridge 11 used for applying the clip according to the invention, as an apparatus suitable for this purpose.

The clamping bars 1, 2 were introduced into the cartridges 11 by way of the insertion openings 21 present on both sides. However, the cartridge 11 can also have insertion openings for the first clamping bar 1 and for the second clamping bar 2, in each instance, separate from one another. The clamping bar 2 can be horizontally displaced by means of the plunger 14, and the tissue clamp formed after it is joined together with the first clamping bar 1, with the inclusion of organic tissue, can be ejected. At its proximal end, the cartridge 11 is configured in the form of a sheathing tube section 17. The cartridge 11 is equipped with the plunger 14 by means of the sheathing tube section 17. On the other hand, the sheathing tube section 17 serves for coupling with the applicator, not shown here, as the handling instrument. For this purpose, the tubular end of the applicator, configured for a bayonet closure, is pushed onto the sheathing tube section 17 up to the stop 15, and positioned in stable manner by means of the fixation element 16.

Figure 9:
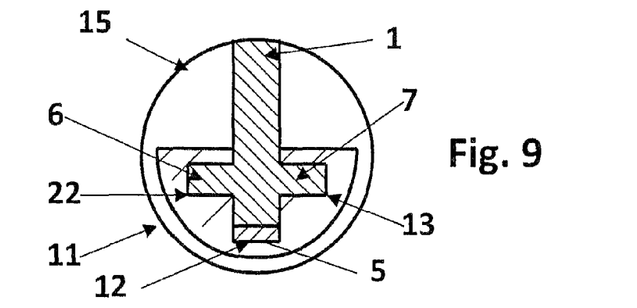
FIG. 9 the front view of the cartridge according to FIG. 8.

FIG. 9 schematically shows the front view of the cartridge 11 according to FIG. 8 equipped with a clip according to FIG. 1. The first clamping bar 1 is positioned in the grooves 13 and 22 of the cartridge 11 and guided in them. The shank 5 of the second clamping bar 2 slides on the bed 12 of the cartridge 11. It can be clearly seen that the groove 13 and the groove 22 are structured to be continuous and open toward the distal end of the cartridge 11. In order to guarantee the pressure clamping of the first clamping bar 1 in the cartridge 11, in this exemplary embodiment the clear width formed by the groove 13 and the groove 22 decreases in the direction of the distal end of the cartridge 11. In such an embodiment of the cartridge 11 according to FIG. 7, the distal end of the cartridge 11 and/or the shoulders 6, 7 of the clamping bars 1, 2 can be formed from an elastic material, to support the pressure clamping. The pressure clamping of the first clamping bar 1 can also already be achieved solely by means of formed and vertically running ribs that engage into matching recesses in the guide grooves 13, 22 or the shoulders 6, 7.

Figure 10A:
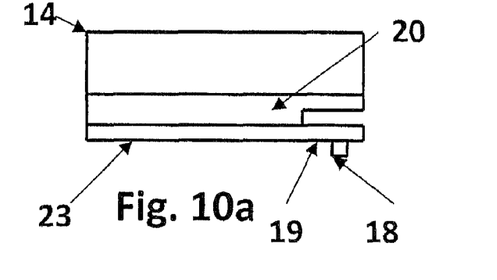
FIG. 10*a* the side view of a plunger.
Figure 10B:
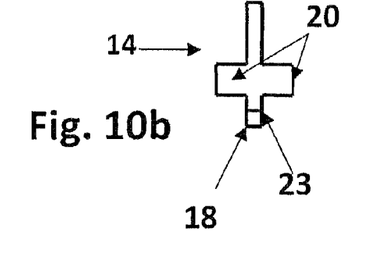
FIG. 10*b* the front view of the plunger according to FIG. 10*a*.

A plunger 14 that can be used for the cartridge 11 is shown schematically in a side view in FIG. 10a and in the front view of the latter in FIG. 10b. The plunger 14 has the shoulders 20 on both sides, which can also be mounted in the grooves 13 and 22 and guided in them by means of the applicator, not shown. For secure initial positioning of the plunger 14 in the sheathing tube section 17, the lower crosspiece 23 of the plunger 14 can have a resiliently configured tongue 19 that engages, by means of the fixation element 18, into a corresponding recess of the sheathing tube section 17, not shown here. In order to prevent ejection of the plunger 14 from the cartridge 11 together with the tissue clamp, the cartridge 11 has a further recess, also not shown here, at its bottom between the distal end and the stop 15 configured as a ring-shaped bead, into which recess the fixation element 18 engages after ejection of the tissue clamp, so that the plunger 14 cannot be ejected.

REFERENCE SYMBOL LIST 1 clamping bar;
2 clamping bar;
3 holding bore;
4 holding pin;
5 shank;
6 shoulder;
7 shoulder;
8 recess;
9 clamping surface;
10 ribbing
11 cartridge
12 cartridge bed
13 groove
14 plunger
15 stop
16 fixation element
17 sheathing tube section
18 fixation element
19 spring tongue
20 shoulder
21 insertion opening
22 groove
23 crosspiece

The invention claimed is:

1. A surgical clip for minimally invasive surgery, for clamping off organic tissue, to form a tissue clamp consisting of a first clamping bar corresponding to a second clamping bar, the first clamping bar having a length that is different from a length of the second clamping bar, wherein the first clamping bar and the second clamping bar, at their base, on both sides, have shoulders for being guided in grooves of a cartridge, in each instance, and one clamping bar has a continuous holding bore into which a holding pin provided on the other clamping bar engages for clamping off the organic tissue, with force fit and shape fit, wherein the first clamping bar (1) is positioned at a distal end of the cartridge (11);

the second clamping bar (2) can be joined together with the first clamping bar (1), in one plane with the first clamping bar (1), in infinitely adjustable manner, with pressure clamping of the tissue;

the clamping bar having the greater length possesses a shank (5) at its lower end, said shank extending out from the clamping bar in a direction toward the clamping bar having a shorter length, which shank, during joining together with the other clamping bar (1; 2) clamping off the organic tissue, pushes itself, with shape fit, under the shorter other clamping bar (1; 2), and thereby gives the tissue clamp significant additional stability;

a plunger (14) is mounted in the cartridge (11) for displacement of the second clamping bar (2) and for ejection of the tissue clamp, and the cartridge (11) has means for a releasable connection with an applicator at its proximal end;

the grooves (13; 22) are configured to be open toward the distal end of the cartridge (11);

the first clamping bar (1) and the second clamping bar (2), with the shoulders (6; 7), in each instance, consist of a resorbable material, a clear width between the grooves (13,22) in which the shoulders (6; 7) are stored and guided decreases in a direction of the distal end of the cartridge (11).

2. The surgical clip according to claim 1, wherein the shoulders (6) of the first clamping bar (1) are configured to be flattened toward the distal end, over their entire length or only in part, corresponding, in each instance, with the reduction in the clear width between the grooves (13; 22) of the cartridge (11).

3. The surgical clip according to claim 1, wherein a clamping surface (8) of the first clamping bar (1) and that of the second clamping bar (2; 14) are configured to be roughened or corrugated.

4. The surgical clip according to claim 1, wherein a clamping surface (8) of the first clamping bar (1) and the clamping surface (8) of the corresponding second clamping bar (2) are configured in step shape.

5. The surgical clip according to claim 1, wherein the shank (5) has a length that corresponds to at least a longitudinal width of the corresponding first clamping bar (1) at the base of the first clamping bar.

6. The surgical clip according to claim 1, wherein the shoulders (6) of the first clamping bar (1) have vertically running ribbings (10).

7. The surgical clip according to claim 1, wherein the clamping pressure of the first clamping bar (1) is brought about by a reduction in the clear width between the guide grooves (13; 22) that runs in the direction of the distal end of the cartridge (11) and/or by means of ribs (10) of the shoulders (6) of the first clamping bar (1) that engage into recesses that are provided for this purpose in the guide grooves (13; 22) at the distal end of the cartridge (11).

8. The surgical clip according to claim 1, wherein a width of the shank (5) corresponds to a width of a bed (12) of the cartridge (11).

9. The surgical clip according to claim 1, wherein the shoulders (6; 7) of the first clamping bar (1) and of the second clamping bar (2) demonstrate an elasticity such that the tissue clamp can be ejected by pressing pressure, even with rigid distal ends of the cartridge (11), without damage.

10. The surgical clip according to claim 1, wherein the shoulders (6; 7) of the first clamping bar (1) and of the second clamping bar (2) consist of a non-elastic material, and wherein the distal end of the cartridge (11) is configured to be elastic and thereby allows ejection of the tissue clamp without damage.

11. The surgical clip according to claim 1, wherein the means for the releasable connection with the applicator are a stop (15) and a fixation element (16) provided at the lower end of a sheathing tube section (17) of the cartridge (11) for accommodation of the applicator by means of a bayonet closure or wherein the means are engagement elements.

12. The surgical clip according to claim 1, wherein the plunger (14) has a fixation element (18) that engages into corresponding recesses when the surgical clip is handled, which recesses are provided in a bottom of a sheathing tube section (17), at a distance from one another in a longitudinal direction.

13. The surgical clip according to claim 1, wherein clamping surfaces of the clamping bars are configured to be concave.

* * * * *